US010583052B2

(12) United States Patent
Lee et al.

(10) Patent No.: US 10,583,052 B2
(45) Date of Patent: Mar. 10, 2020

(54) SUPERABSORBENT POLYMER COMPOSITION

(71) Applicant: LG Chem, Ltd., Seoul (KR)

(72) Inventors: Jin Woo Lee, Daejeon (KR); Young Sam Kim, Daejeon (KR); Young In Yang, Daejeon (KR); Su Jin Kim, Daejeon (KR)

(73) Assignee: LG Chem, Ltd. (KR)

( * ) Notice: Subject to any disclaimer, the term of this patent is extended or adjusted under 35 U.S.C. 154(b) by 225 days.

(21) Appl. No.: 15/751,705

(22) PCT Filed: Dec. 1, 2016

(86) PCT No.: PCT/KR2016/014057
§ 371 (c)(1),
(2) Date: Feb. 9, 2018

(87) PCT Pub. No.: WO2017/099422
PCT Pub. Date: Jun. 15, 2017

(65) Prior Publication Data
US 2018/0228670 A1 Aug. 16, 2018

(30) Foreign Application Priority Data

Dec. 9, 2015 (KR) .................. 10-2015-0175006
Nov. 30, 2016 (KR) .................. 10-2016-0162033

(51) Int. Cl.
A61L 15/46 (2006.01)
B01J 20/26 (2006.01)
A61F 13/53 (2006.01)
C08L 101/00 (2006.01)
A61L 15/18 (2006.01)
C08J 3/12 (2006.01)
A61L 15/20 (2006.01)
C08K 9/12 (2006.01)
A61L 15/60 (2006.01)
A61L 15/42 (2006.01)
C08K 3/22 (2006.01)
C08K 7/18 (2006.01)
C08K 5/09 (2006.01)
C08K 3/08 (2006.01)

(52) U.S. Cl.
CPC .............. A61F 13/53 (2013.01); A61L 15/18 (2013.01); A61L 15/20 (2013.01); A61L 15/42 (2013.01); A61L 15/46 (2013.01); A61L 15/60 (2013.01); C08J 3/128 (2013.01); C08K 3/22 (2013.01); C08K 7/18 (2013.01); C08K 9/12 (2013.01); C08L 101/00 (2013.01); A61F 2013/530569 (2013.01); A61F 2013/530671 (2013.01); C08J 2300/14 (2013.01); C08J 2333/02 (2013.01); C08K 5/09 (2013.01); C08K 2003/0812 (2013.01); C08K 2201/003 (2013.01)

(58) Field of Classification Search
CPC ........ C08J 3/128; C08J 2300/14; A61F 13/53; A61F 15/60; A61F 15/42; A61F 15/46
See application file for complete search history.

(56) References Cited

U.S. PATENT DOCUMENTS

| 6,096,299 | A | 8/2000 | Guarracino et al. |
| 6,663,949 | B1 | 12/2003 | Tanaka et al. |
| 7,662,354 | B2 | 2/2010 | Oki |
| 2003/0124171 | A1 | 7/2003 | Sun et al. |
| 2004/0120921 | A1 | 6/2004 | Quincy et al. |
| 2005/0245393 | A1* | 11/2005 | Herfert ................... A61L 15/60 502/402 |
| 2007/0060691 | A1 | 3/2007 | Kim |
| 2014/0330229 | A1 | 11/2014 | Lee |
| 2015/0252130 | A1 | 9/2015 | Loick et al. |
| 2016/0051423 | A1 | 2/2016 | Ota et al. |

FOREIGN PATENT DOCUMENTS

| JP | 3458808 | B2 | 10/2003 |
| JP | 3558126 | B2 | 8/2004 |
| JP | 3587738 | B2 | 11/2004 |
| JP | 2005194376 | A * | 7/2005 |
| JP | 2005194376 | A | 7/2005 |
| JP | 3757679 | B2 | 3/2006 |
| JP | 4638333 | B2 | 2/2011 |
| JP | 4721899 | B2 | 7/2011 |
| JP | 2014204799 | A | 10/2014 |
| KR | 100193698 | B1 * | 6/1999 ......... A61F 13/8405 |
| KR | 100193698 | B1 | 6/1999 |

(Continued)

OTHER PUBLICATIONS

Extended European Search Report for Application No. EP16873287.3 dated Sep. 7, 2018.
Bertazzo et al., "Control of a-Alumina Surface Charge with Carboxylic Acids", Langmuir Article, American Chemical Society, Recieved Aug. 23, 2009, vol. 26, No. 5, pp. 3364-3371.
International Search Report for Application No. PCT/KR2016/014057 dated Mar. 7, 2017.

Primary Examiner — Kara B Boyle
(74) Attorney, Agent, or Firm — Lerner, David, Littenberg, Krumholz & Mentlik, LLP

(57) ABSTRACT

The present invention relates to a superabsorbent polymer composition. Since the superabsorbent polymer composition comprises aluminosilicate particles capable of effectively adsorbing and decreasing compounds inducing odor in sanitary products such as a diaper, etc. without deterioration of the properties of superabsorbent polymer such as centrifugal retention capacity, absorbency under load, and penetration, and does not induce caking, it can be usefully used in sanitary products, etc.

9 Claims, No Drawings

(56) References Cited

FOREIGN PATENT DOCUMENTS

| KR | 100214444 B1 | | 8/1999 | |
|---|---|---|---|---|
| KR | 20040070235 A | | 8/2004 | |
| KR | 20100096376 A | | 9/2010 | |
| KR | 20120102388 A | | 9/2012 | |
| KR | 20140126821 A | * | 11/2014 | |
| KR | 20140126821 A | | 11/2014 | |
| WO | 9112031 A1 | | 8/1991 | |
| WO | WO-0168156 A1 | * | 9/2001 | ............ A61L 15/18 |
| WO | 2015054463 A1 | | 4/2015 | |

* cited by examiner

SUPERABSORBENT POLYMER COMPOSITION

CROSS-REFERENCE TO RELATED APPLICATION

The present application is a national phase entry under 35 U.S.C § 371 of International Application No. PCT/KR2016/014057, filed Dec. 1, 2016, published in Korean, which claims priority from Korean Patent Application Nos. 10-2015-0175006 filed on Dec. 9 2015 and 10-2016-0162033 filed Nov. 30, 2016, with the Korean Intellectual Property Office, the disclosures of which are incorporated herein by reference in their entireties.

BACKGROUND OF THE INVENTION (a) Field of the Invention

The present invention relates to a superabsorbent polymer composition.

(b) Description of the Related Art

Super absorbent polymer (SAP) is synthetic polymer material that can absorb moisture of 500 to 1000 times of self-weight, and is also named differently as super absorbency material (SAM), absorbent gel material (AGM), etc. according to developing companies. The superabsorbent polymer began to be commercialized as sanitary items, and currently, it is being widely used as hygienic goods such as a disposable diaper and so on, water-holding material for soil, water stop material for civil engineering and architecture, sheets for raising seedling, freshness preservatives in the field of food circulation, fomentation material, etc.

Sanitary products or disposable absorption products such as a paper diaper for children require a function of effectively reducing unpleasant odor involved in the excretion of body liquid such as urine, etc. as well as absorptivity. Since the cause of unpleasant odor is mostly in ammonia produced by decomposition of urea in urine by bacteria, odor may be significantly reduced if ammonia is removed.

For this, a method of mixing superabsorbent polymer with porous adsorption material has been developed.

However, if the porous adsorption material is mixed with superabsorbent polymer, although odor reducing effect may be obtained, the properties of superabsorbent polymer such as absorptivity or penetration may be deteriorated, or caking wherein superabsorbent polymers are agglomerated or hardened as time elapses may occur.

SUMMARY OF THE INVENTION

Therefore, it is an object of the present invention to provide a superabsorbent polymer composition that exhibits excellent deodorant effect, does not hinder the properties of superabsorbent polymer, and particularly, can reduce caking.

In order to overcome the object, the present invention provides a superabsorbent polymer composition comprising:

a superabsorbent polymer formed by the polymerization of water-soluble ethylenically unsaturated monomers comprising an acid group, of which at least a part is neutralized; and aluminosilicate particles having a bulk density of 0.900 to 1.000 $g/cm^3$, on which organic acid is supported.

The superabsorbent polymer composition comprises aluminosilicate particles on which organic acid is supported, as a deodorant capable of effectively adsorbing and decreasing compounds inducing odor in sanitary products such as a diaper, etc., particularly ammonia component, without deterioration of the properties of superabsorbent polymer such as centrifugal retention capacity, absorbency under load, and penetration. And, even if it comprises the deodorant, it does not induce caking wherein superabsorbent polymers are agglomerated with each other, and thus, can be usefully applied in sanitary products, etc.

DETAILED DESCRIPTION OF THE EMBODIMENTS

Technical terms in the present specification are only for mentioning specific embodiments, and they are not intended to restrict the present invention unless there is a particular mention about them. The singular expressions used herein may include the plural expressions unless they are differently expressed contextually. The meaning of the term "include" used in the specification embodies specific characteristics, areas, essences, steps, actions, elements, and/or components, and does not exclude existence or addition of other specific characteristics, areas, essences, steps, actions, elements, components, and/or groups.

Although various modifications can be made to the present invention and the present invention may have various forms, specific examples will be illustrated and explained in detail below. However, it should be understood that these are not intended to limit the present invention to specific disclosure, and that the present invention includes all the modifications, equivalents or replacements thereof without departing from the spirit and technical scope of the invention.

Hereinafter, a superabsorbent polymer composition according to specific embodiment of the invention will be explained in detail.

The superabsorbent polymer composition according to one embodiment of the present invention comprises superabsorbent polymer formed by the polymerization of water-soluble ethylenically unsaturated monomers comprising an acid group, of which at least a part is neutralized; and aluminosilicate particles having a bulk density of 0.900 to 1.000 $g/cm^3$, on which organic acid is supported.

The aluminosilicate particles on which organic acid is supported, which is included in the superabsorbent polymer composition of the present invention, has a bulk density of about 0.900 to about 1.000 $g/cm^3$, or about 0.900 to about 0.980 $g/cm^3$, or about 0.900 to about 0.960 $g/cm^3$, or about 0.910 to about 0.950 $g/cm^3$.

Since the aluminosilicate particles on which organic acid is supported of the present invention has the above bulk density, it can selectively and efficiently adsorb components inducing unpleasant odor such as ammonia thus physically/chemically removing the same, and exhibit excellent deodorant effect.

According to one embodiment of the present invention, the aluminosilicate particles on which organic acid is supported comprises particles having a particle diameter of 45 μm or more and less than 600 μm in the content of about 80 to about 99.99 wt %, or about 90 to about 99.99 wt %, or about 92 to about 99.99 wt %, or about 95 to about 99.99 wt %.

And, according to one embodiment of the present invention, the aluminosilicate particles on which organic acid is supported comprises particles having a particle diameter of 300 μm or more and less than 600 μm in the content of about 50 to about 80 wt %, or about 60 to about 80 wt %, or about 70 to about 80 wt %.

And, according to one embodiment of the present invention, the aluminosilicate particles on which organic acid is supported comprises particles having a particle diameter of less than 45 μm only in a very small amount such as less than about 0.5 wt %, or less than about 0.3 wt %, or less than about 0.2 wt %.

Since the aluminosilicate particles on which organic acid is supported has the above particle diameter distribution, it can adsorb components inducing unpleasant odor more selectively and efficiently, and physically/chemically removing the same, thus exhibiting excellent deodorant effect, and when mixed with superabsorbent polymer, it may exhibit anti-caking performance.

The aluminosilicate particles on which organic acid is supported of the present invention comprise organic acid in the content of about 0.001 to about 65 wt %, or about 10 to about 50 wt %, or about 20 to about 40 wt %, based on the total weight of the aluminosilicate particles. Thus, the aluminosilicate particles have an appropriate number of acid sites inside and/or on the surface. In case the acid sites are included inside and/or on the surface of the aluminosilicate particles, they physically adsorb ammonia components, and besides, the hydrogen cation ($H^+$) of the acid sites bind with ammonia to form ammonium salts, thus rendering ammonia inert, thereby effectively achieving the removal of ammonia components.

The organic acid may include one or more selected from the group consisting of citric acid, fumaric acid, maleic acid and lactic acid, but is not limited thereto.

According to one embodiment of the present invention, the aluminosilicate particles on which organic acid is supported may further comprise silica. In case the silica is used to coat on the surface of the aluminosilicate particles on which organic acid is supported, hygroscopicity may be lowered and the agglomeration of the aluminosilicate particles on which organic acid is supported may be prevented, thus further increasing the anti-caking effect.

The above-explained aluminosilicate particles on which organic acid is supported may be mixed with superabsorbent polymer formed by the polymerization of water-soluble ethylenically unsaturated monomers and applied in sanitary products such as a diaper, etc.

According to one embodiment of the present invention, the aluminosilicate particles on which organic acid is supported may be included in the content of about 1 to about 10 parts by weight, or about 1 to about 5 parts by weight, or about 1 to about 3 parts by weight, based on 100 parts by weight of the superabsorbent polymer. If the amount of the aluminosilicate particles is too small, deodorant effect may be slight, and if it is too large, there is a concern of hindering the properties of superabsorbent polymer, and thus, the above content range may be appropriate.

The aluminosilicate particles on which organic acid is supported may be prepared by dissolving organic acid in purified water to prepare an acid solution; introducing metal silicate and aluminium sulfate into the acid solution to prepare a mixture; stirring the mixture to react; and filtering and drying the reactant.

According to one embodiment of the present invention, the organic acid may include one or more selected from the group consisting of citric acid, fumaric acid, maleic acid and lactic acid, but is not limited thereto.

According to one embodiment of the present invention, the organic acid may be dissolved in the content of about 10 to about 50 parts by weight, or about 10 to about 30 parts by weight, based on 100 parts by weight of purified water.

In the acid solution in which the organic acid is completely dissolved, metal silicate and aluminium sulfate are introduced to obtain a mixture. As the metal silicate, sodium silicate may be preferably used.

The mixture of the acid solution, metal silicate and aluminium sulfate is stirred while raising temperature, to progress a reaction. Here, the temperature may be in the range of about 80 to about 120° C., or about 80 to about 110° C., and the stirring may be conducted for about 1 to about 5 hours, or about 2 to about 4 hours so as to sufficiently progress the reaction, but not limited thereto.

By the above described reaction, the aluminosilicate particles on which organic acid is supported of the present invention may be obtained, and by controlling the reaction conditions such as the contents of purified water, organic acid, metal silicate and aluminium sulfate, reaction temperature, etc., or sieving with a sieve, the particle diameter distribution of the aluminosilicate particles on which organic acid is supported may be adjusted in the above explained range.

Thereafter, the temperature of the reactant is decreased to room temperature, and the reactant is filtered and dried to obtain aluminosilicate particles on which organic acid is supported in the form of dry powder.

According to one embodiment of the present invention, a process of mixing the obtained aluminosilicate particles on which organic acid is supported with silica may be further conducted. The amount of the silica used is not specifically limited, but for example, it may be mixed in the content rage of about 0.1 to about 10 parts by weight, based on 100 parts by weight of the aluminosilicate particles.

Meanwhile, the kind or preparation method of the superabsorbent polymer mixed with the aluminosilicate particles on which organic acid is supported may be those commonly used in corresponding technical field, and the step and method of mixing the superabsorbent polymer with aluminosilicate particles on which organic acid is supported are not specifically limited.

For example, the superabsorbent polymer may be obtained by carrying out thermal polymerization or photo-polymerization of a monomer composition comprising water-soluble ethylenically unsaturated monomers and a polymerization initiator to obtain hydrogel polymer, and drying, grinding sieving, etc. the hydrogel polymer, and if necessary, s surface crosslinking or powder reassembly process may be further conducted.

For reference, throughout the specification, "superabsorbent polymer" means crosslinked polymer formed by the polymerization of water-soluble ethylenically unsaturated monomers comprising acid groups, of which at least a part are neutralized, or base resin made in the form of powder by drying and grinding the crosslinked polymer, or it is used to include those made appropriate for productization through additional processes of the crosslinked polymer or base resin, for example, surface crosslinking, powder reassembly, grinding, sieving, etc.

As the water-soluble ethylenically unsaturated monomers, monomers commonly used in the preparation of superabsorbent polymer may be used without limitation in the constructions. Largely, one or more selected from the group consisting of anionic monomers and salts thereof, non-ionic hydrophilic containing monomers, and amino group containing unsaturated monomers and quaternarized products thereof may be used.

Specifically, as the water-soluble ethylenically unsaturated monomers, one or more selected from the group consisting of anionic monomers and salts thereof such as methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid or 2-(meth)acrylamide-2-methyl propane sulfonic acid; non-ionic hydrophilic group containing monomers such as (meth)acrylamide, N-substituted (meth)acrylate, 2-hydroxyethyl (meth)acrylate, 2-hydroxypropyl (meth) acrylate, methoxy polyethylene glycol (meth)acrylate, or polyethylene glycol (meth)acrylate; and amino group containing unsaturated monomers such as (N,N)-dimethylaminoethyl (meth)acrylate, (N,N)-dimethylaminopropyl (meth) acrylamide, and quaternarized products thereof, may be preferably used.

More preferably, acrylic acid or salts thereof, for example, acrylic acid and/or alkali metal salts such as a sodium salt thereof may be used, and by using such monomers, superabsorbent polymer having more excellent properties can be prepared. In case the alkali metal salt of acrylic acid is used as monomers, the acrylic acid may be neutralized with a basic compound such as caustic soda (NaOH) before use.

The polymerization initiator used in the polymerization of the water-soluble ethylenically unsaturated monomers is not specifically limited as long as it is commonly used for the preparation of superabsorbent polymer.

Specifically, as the polymerization initiators, a thermal polymerization initiator or a photopolymerization initiator according to UV irradiation may be used according to polymerization methods. However, even in the case of photopolymerization, since a certain amount of heat is generated by UV irradiation, etc., and heat is generated to some degree according to the progression of an exothermic polymerization reaction, a thermal polymerization initiator may be additionally included.

The photopolymerization initiator is not limited in terms of its construction, as long as it is a compound capable of forming a radical by light such as UV.

According to one embodiment of the present invention, the monomer composition may further comprise an internal crosslinking agent as the raw material of superabsorbent polymer. As the internal crosslinking agent, a crosslinking agent that has one or more functional groups capable of reacting with the water-soluble substituent of the water-soluble ethylenically unsaturated monomers, and has one or more ethylenically unsaturated groups; or a crosslinking agent that has two or more functional groups capable of reacting with the water-soluble substituent of the monomers and/or water-soluble substituent formed by the hydrolysis of the monomers may be used.

Specific examples of the internal crosslinking agent may include C8-C12 bisacrylamide, bismetharylamide, poly (meth)acrylate of C2-C10 polyol or poly(meth)allylether of C2-C10 polyol, etc., and more specifically, one or more selected from the group consisting of N,N'-methylenebis (meth)acrylate, ethyleneoxy(meth)acrylate, polyethyleneoxy(meth)acrylate, propyleneoxy(meth)acrylate, glycerin diacrylate, glycerin triacrylate, trimethylol triacrylate, triallylamine, triarylcyanurate, triallylisocyanate, polyethyleneglycol, diethyleneglycol and propyleneglycol may be used.

In the preparation method of the preset invention, the monomer composition of superabsorbent polymer may further comprise additives such as a thickener, a plasticizer, a preservation stabilizer, an antioxidant, etc., as necessary.

The above explained raw materials such as water-soluble ethylenically unsaturated monomers, photopolymerization initiator, thermal polymerization initiator, internal cross linking agent and additives may be provided in the form of a monomer composition solution dissolved in a solvent.

Meanwhile, a method of forming hydrogel polymer by the thermal polymerization or photopolymerization of the monomer composition is not specifically limited in terms of its construction, as long as it is a commonly used polymerization method.

Specifically, the polymerization method is largely classified into thermal polymerization and photopolymerization according to energy source, and commonly, thermal polymerization may be progressed in a reactor equipped with a stirring axis such as a kneader, and photopolymerization may be progressed in a reactor equipped with a movable conveyer belt, but the above explained polymerization methods are no more than examples, and the present invention is not limited thereto.

Here, the moisture content of the obtained hydrogel polymer may be 40 to 80 wt %. Throughout the specification, the "moisture content" is the content of moisture occupied based on the total weight of hydrogel polymer, and it means a value obtained by subtracting the weight of polymer of a dry state from the weight of hydrogel polymer. Specifically, it is defined as a value calculated by measuring the weight loss according to moisture evaporation in the polymer while raising the temperature of polymer through infrared heating to dry. At this time, the drying condition is established such that the temperature is raised from room temperature to about 180° C. and then maintained at 180° C., and the total drying time is 20 minutes including a temperature raising step of 5 minutes.

Next, the obtained hydrogel polymer is dried.

At this time, if necessary, in order to increase the efficiency of the drying step, a step of coarse grinding may be conducted before drying.

Here, grinders that can be used in the coarse grinding is not limited in terms of the constructions, but specifically, one selected from the group consisting of a vertical pulverizer, a turbo cutter, a turbo grinder, a rotary cutter mill, a cutter mill, a disc mill, a shred crusher, a crusher, a chopper, a disc cutter may be used, but is not limited thereto.

The coarse grinding step may be progressed such that the particle diameter of hydrogel polymer may become about 2 to about 10 mm.

The hydrogel polymer coarsely ground as explained above, or hydrogel polymer that does not pass through the coarse grinding step is dried.

And, the drying method of the drying step is not limited in terms of the construction as long as it can be commonly used as a drying process of hydrogel polymer. Specifically, in the drying step, hot wind supply, infrared ray irradiation, ultrahigh frequency wave irradiation, or UV irradiation, etc., may be applied. The polymer dried by such a method may exhibit a moisture content of about 0.1 to about 10 wt %.

Next, a step of grinding the dried polymer obtained through the drying step is progressed.

The weight average particle diameter of the polymer powder obtained after the grinding step may be about 150 μm to about 850 μm. As a grinder for grinding to such a particle diameter, specifically, a pin mill, a hammer mill, a screw mill, a roll mill, a disc mill, or a jog mill, etc. may be used, but the grinder is not limited thereto.

And, in order to manage the properties of the finally productized superabsorbent polymer after the grinding step, a step of sieving the polymer powder obtained after grinding according to the particle diameter may be conducted. Preferably, polymer with a particle diameter of about 150 μm to about 850 μm may be sieved.

According to one embodiment of the present invention, a step of surface crosslinking of the ground or sieved polymer may be further conducted. Here, as the surface crosslinking agent, compounds capable of reacting with the functional group of the polymer may be used without limitation in the construction.

The superabsorbent polymer obtained by the above described process and the above explained aluminosilicate particles on which organic acid is supported are uniformly mixed to obtain the superabsorbent polymer composition of the present invention.

Here, a method of mixing is not specifically limited, and for example, superabsorbent polymer and aluminosilicate particles may be put in a reactor and mixed, or a solution comprising aluminosilicate particles may be sprayed to superabsorbent polymer, or superabsorbent polymer and aluminosilicate particles may be continuously fed to a continuously operated reactor such as mixer to mix them.

The above obtained superabsorbent polymer composition of the present invention exhibits excellent deodorant effect and anti-caking effect.

For example, when 1 g of the superabsorbent polymer composition of a dry state is put in a bag of 3 L volume, and then, 100 ppm of ammonia gas is introduced into the bag, and after 30 minuets, the removal rate of ammonia is measured, the removal rate of ammonia may be 80% or more, 80% to 100%, or 90% to 100%.

And, when 1 g of the superabsorbent polymer of a dry state is swollen with 30 g of a saline solution (0.9 wt % NaCl solution) for 30 minutes and 0.5 g of the superabsorbent polymer of a swollen gel state is put into a bag of 3 L volume, and then, 500 ppm of ammonia gas is introduced into the bag, and after 30 minutes, the removal rate of ammonia gas is measured, the removal rate of ammonia gas may be 90% or more, 90% to 100%, or 94% to 99%.

Hereinafter, the actions and effects of the present invention will be explained through specific examples in more detail. However, these examples are presented only as the illustrations of the invention, and the scope of the invention is not determined thereby.

EXAMPLE

Preparation Example: Preparation of Aluminosilicate Particles on which Organic Acid is Supported

Preparation Example 1

In 37.5 mL of purified water, 7.5 g of citric acid was introduced and completely dissolved. After citric acid was completely dissolved, 122.7 g of sodium silicate, and 8.6 g of aluminium sulfate were introduced, and the reaction temperature was raised to 100° C., and then, they were reacted while stirring at 150 rpm for 3 hours.

After the reaction was finished, when the temperature dropped to room temperature, the reaction mixture was filtered using a filter, and washed with 500 mL of water to remove impurities. The product was dried at 130° C. for 6 hours using a dry oven to obtain aluminosilicate particles on which citric acid is supported, having moisture content within 5%, in the form of solid powder.

The solid powder was sieved with a sieve to the particle size distribution of the following Table 1.

Preparation Example 2

Based on 100 parts by weight of the solid powder obtained by sieving in Preparation Example 1, 0.3 parts by weight of silica was used to coat the surface.

Comparative Preparation Example 1

The solid powder obtained in Preparation Example 1 was sieved with a sieve to the particle size distribution in the following Table 1.

Comparative Preparation Example 2

Aluminosilicate particles were prepared by the same method as Preparation Example 1, except that citric acid was not used.

For each aluminosilicate particles obtained in Preparation Examples 1 and 2 and Comparative Preparation Examples 1 and 2, particle size distribution and bulk density were measured and shown in the following Table 1. The bulk density was measured according to WSP 260.2 method.

TABLE 1

|  |  | Preparation Example 1 | Preparation Example 2 | Comparative Preparation Example 1 | Comparative Preparation Example 2 |
|---|---|---|---|---|---|
| Particle size distribution(wt %) | 850 μm or more | 0.1 | 0.2 | 0.2 | 0.1 |
|  | 600 μm or more and less than 850 μm | 0.2 | 0.2 | 0.2 | 0.2 |
|  | 300 μm or more and less than 600 μm | 77.9 | 76.1 | 0.6 | 77.9 |
|  | 150 μm or more and less than 300 μm | 19.6 | 21.3 | 28.8 | 19.6 |
|  | 45 μm or more and less than 150 μm | 1.9 | 2.1 | 49.3 | 1.9 |
|  | Less than 45 μm | 0.1 | 0.1 | 20.8 | 0.1 |

TABLE 1-continued

|  | Preparation Example 1 | Preparation Example_2 | Comparative Preparation Example 1 | Comparative Preparation Example 2 |
|---|---|---|---|---|
| Bulk Density(g/cm$^3$) | 0.945 | 0.918 | 0.463 | 0.945 |
| Organic acid content in aluminosilicate particles (wt %) | 30 | 30 | 30 | 0 |

Example: Preparation of a Superabsorbent Polymer Composition

Example 1

100 parts by weight acrylic acid monomers were mixed with 38.9 parts by weight of caustic soda (NaOH) and 103.9 parts by weight of water, and to the mixture, 0.1 parts by weight of sodium persulfate as a thermal polymerization initiator, 0.01 parts by weight of diphenyl(2,4,6-trimethyl-benzoyl)-phosphine oxide as a photopolymerization initiator and 0.3 parts by weight of polyethyleneglycol diacrylate as a crosslinking agent were added to prepare a monomer composition.

While the monomer composition was flowed on the polymerization belt of a continuous belt polymerization reactor of which internal temperature is maintained at 80° C., and on which a UV irradiation device having an intensity of 10 mW with a mercury UV lamp light source is installed, at a flow rate of 243 kg/hr, UV was irradiated for 1 minute, and a polymerization reaction was progressed under no light source for additional 2 minutes.

The gel type polymerized sheet was primarily cut using a shredder type cutter and coarsely ground through a meat chopper. Thereafter, it was dried through a hot air drier at a temperature of 180° C. for 30 minutes, and then, ground using a rotary mixer, and sieved to 180 μm to 850 μm, thus preparing base resin.

To the base resin, 0.1 wt % of ethylene glycol diglycidyl epoxide was added and uniformly mixed, and then, surface treatment was progressed at 140° C. for 1 hour to obtain superabsorbent polymer 100 parts by weight of the superabsorbent polymer was mixed with 2.5 parts by weight of the aluminosilicate particles of Preparation Example 1, followed by stirring at 500 rpm for 2 minutes.

Example 2

A superabsorbent polymer composition was prepared by the same method as Example 1, except that 2.5 parts by weight of the aluminosilicate particles of Preparation Example 2 was mixed instead of the aluminosilicate particles of Preparation Example 1.

Example 3

A superabsorbent polymer composition was prepared by the same method as Example 1, except that 5 parts by weight of the aluminosilicate particles of Preparation Example 1 was mixed.

Comparative Example 1

A superabsorbent polymer composition was prepared by the same method as Example 1, except that 2.5 parts by weight of the aluminosilicate particles of Comparative Preparation Example 1 was mixed with 100 parts by weight of the superabsorbent polymer instead of the aluminosilicate particles of Preparation Example 1.

Comparative Example 2

A superabsorbent polymer composition was prepared by the same method as Example 1, except that 0.75 parts by weight of citric acid was mixed with 100 parts by weight of the superabsorbent polymer instead of the aluminosilicate particles of Preparation Example 1, followed by stirring with a blender at 500 rpm for 2 minutes.

Comparative Example 3

A superabsorbent polymer composition was prepared by the same method as Example 1, except that 2.5 parts by weight of the aluminosilicate particles of Comparative Preparation Example 2 was mixed instead of the aluminosilicate particles of Preparation Example 1.

Comparative Example 4

The superabsorbent polymer before mixing with aluminosilicate particles, which is the same as used in Example 1, was prepared.

Property Evaluation of Superabsorbent Polymer

For the superabsorbent polymer compositions of Examples 1 to 3 and Comparative Examples 1 to 4, the properties were measured as follows, and the results are shown in Table 2.

(1) Deodorant Performance Test

For the superabsorbent polymer composition, deodorant performance was measured as follows.

First, for each superabsorbent polymer composition of Examples and Comparative Examples, i) 1 g of dry powder state with a moisture content of 2% or less (hereinafter, referred to as a dry sample), and ii) 0.5 g of a swollen gel state, after swelling 1 g of the dry powder in 30 g of a saline solution (0.9 wt % NaCl solution) for 30 minutes (hereinafter, referred to as a wet sample) were taken, and respectively put in a bag of 3 L volume.

A 10 L Flek bag was connected to a nitrogen line to which a flow meter is attached, and then, 10 L of nitrogen (purity 99.99%) was metered and introduced for about 2 minutes. Into the Flek bag containing nitrogen, 25% ammonia water (OCI Company) was introduced at a fixed quantity using a micro syringe (for example: when preparing 100 ppm ammonia gas, about 2.3 μL of ammonia water is introduced). After introducing a fixed quantity of ammonia water, the ammonia water was evaporated using a hot air dryer to prepare ammonia gas.

It was confirmed through a gas-detecting tube (3M Company, 3 La) whether the ammonia gas was prepared at a desired concentration, and it was connected to a 3 L bag containing each sample to introduce the ammonia gas. After introducing 3 L of ammonia gas, the inlet was blocked with a rubber stopper and left. Here, for 0.5 g of the wet sample of gel state, the concentration of introduced ammonia gas was adjusted to 500 ppm, and for 1 g of the dry sample of dry state, the concentration of ammonia gas was adjusted to 10 ppm.

After 30 minutes, the ammonia gas concentration (ppm) remaining in the bag was measured by a detector tube method (KS I 2218, detector tube type gas measuring device), and the removal rate of ammonia gas was calculated according to the following Formula 1.

Ammonia gas removal rate (%)=(concentration of introduced ammonia gas−concentration of ammonia gas remaining after 30 minutes/concentration of introduced ammonia gas)*100     [Formula 1]

(2) Centrifugal Retention Capacity (CRC)

The centrifugal retention capacity was measured according to EDANA method WSP 241.3. 0.2 g of the prepared superabsorbent polymer composition sample was put in a tea bag and precipitated in a 0.9% saline solution for 30 minutes. Thereafter, it was drained at a centrifugal force of 250 G (gravity) for 3 minutes, and then, the amount of the saline solution absorbed was measured.

(3) Absorption Under Pressure (AUP)

The absorption under pressure was measured according to EDANA method WSP 241.3. 0.9 g of the prepared superabsorbent polymer composition sample was put in a cylinder prescribed in EDANA, and a pressure of 0.7 psi was applied with a piston and weight. Thereafter, the amount of a 0.9% saline solution absorbed for 60 minutes was measured.

(4) Vortex 50 ml of a saline solution was put in a 100 ml beaker together with a magnetic bar. The stirring speed was designated as 600 rpm using a stirrer. Simultaneously with introducing 2.0 g of the superabsorbent polymer composition into the saline solution being stirred, the time was measured. When vortex disappeared in the beaker, the measurement of time was finished.

(5) Flowability

The superabsorbent polymer composition was properly mixed so that particle size may be uniformly mixed, and then, 100±0.5 g of the sample was taken and poured into a 250 ml beaker.

At the bottom of a funnel, a cup for measuring density was positioned at the center, and then, the funnel hole was blocked and the above metered sample was lightly poured into the funnel and filled. As soon as the blocked funnel hole was opened, a stop watch was operated to measure a time taken until the whole sample came down to the lowermost part of the funnel.

All the process was progressed in a steady temperature and humidity room (temperature 23±2° C., relative humidity 45±10%).

(6) Caking Test

To 100 g of the superabsorbent polymer composition, a load of about 5,300 g (2.66 psi) was applied for 1 hour, and then, the cylinder was raised to confirm the degree of agglomeration with naked eyes.

Thereafter, while increasing the pressurization time to 14 hours, 24 hours, 40 hours and 65 hours, the degree of agglomeration was confirmed according to time elapse, and designated as no agglomeration (⊚), very small agglomeration (○), small agglomeration Δ), and large agglomeration (X). If a large quantity of agglomeration was generated on the way, no more pressurization was conducted.

TABLE 2

| | | Example 1 | Example 2 | Example 3 | Comparative Example 1 | Comparative Example 2 | Comparative Example 3 | Comparative Example 4 |
|---|---|---|---|---|---|---|---|---|
| CRC(g/g) | | 35.0 | 35.5 | 34.2 | 34.2 | 36.3 | 35.35 | 36.9 |
| 0.7 Psi AUP(g/g) | | 21.5 | 21.7 | 15.7 | 15.7 | 22.1 | 21.3 | 22.9 |
| Vortex(sec) | | 89 | 90 | 85 | 85 | 92 | 93 | 80 |
| Bulk Density(g/cm$^3$) | | 0.68 | 0.69 | 0.72 | 0.72 | 0.69 | 0.68 | 0.68 |
| Flowability (sec) | | 9.1 | 9.1 | 8.2 | 8.2 | 9.6 | 9.3 | 9.7 |
| PSD (wt %) | 850 μm or more | 0 | 0 | 0 | 0 | 0 | 0 | 0.4 |
| | 600 μm or more and less than 850 μm | 4.8 | 5.1 | 5.5 | 5.5 | 4.9 | 5.2 | 5.7 |
| | 300 μm or more and less than 600 μm | 72.6 | 73.5 | 69.9 | 69.9 | 71.9 | 73.1 | 72.9 |
| | 150 μm or more and less than 300 μm | 21.4 | 20.2 | 22.1 | 22.1 | 22.2 | 20.4 | 19.8 |
| | less than 150 μm | 1.2 | 1.0 | 2.5 | 2.5 | 1.0 | 1.3 | 1.3 |
| Ammonia gas removal rate (%) | Dry sample 100 ppm ammonia | 80 | 100 | 100 | 95 | 35 | 55 | 20 |
| | Wet sample 500 ppm ammonia | 94 | 98 | 98 | 96 | 85 | 91 | 80 |
| Caking Test | 1 hr | ⊚ | ⊚ | ⊚ | ○ | ⊚ | ⊚ | ○ |
| | 14 hr | ⊚ | ⊚ | ○ | Δ | ○ | ⊚ | Δ |
| | 24 hr | ⊚ | ⊚ | ○ | Δ | Δ | Δ | Δ |
| | 40 hr | ○ | ⊚ | Δ | X | X | X | X |
| | 65 hr | Δ | ⊚ | X | | | | |

Referring to Table 2, the superabsorbent polymer composition comprising aluminosilicate particles of the present invention exhibited excellent deodorant effect and absorptivity. And, it is expected to be advantageous for transfer or use of the product because caking is hardly generated even if time elapses. In the case of porous particles used as a deodorant, in general, as the particle size is smaller, the surface area becomes wider and deodorant effect is better, but particles having small particle diameters are highly likely to generate fine particles or caking, and tend to adversely influence the other properties of superabsorbent polymer such as CRC, AUP, etc. However, the aluminosilicate particles and superabsorbent polymer comprising the same of the present invention minimize property deterioration of superabsorbent polymer, and achieve both deodorant effect and anti-caking effect, thus overcoming the above disadvantages.

What is claimed is:

1. A superabsorbent polymer composition comprising:
a superabsorbent polymer formed by the polymerization of water-soluble ethylenically unsaturated monomers comprising acid groups, of which at least a part are neutralized; and
aluminosilicate particles having a bulk density of 0.900 to 1.000 g/cm$^3$, on which organic acid is supported.

2. The superabsorbent polymer composition according to claim 1, wherein, the organic acid is included in the content of 0.001 to 65 wt %, based on the total weight of the aluminosilicate particles on which organic acid is supported.

3. The superabsorbent polymer composition according to claim 1, wherein the aluminosilicate particles on which organic acid is supported comprise particles having a particle diameter of 300 μm or more and less than 600 μm in the content of 50 to 80 wt %, based on the total weight of the aluminosilicate particles.

4. The superabsorbent polymer composition according to claim 1, wherein the aluminosilicate particles on which organic acid is supported comprise particles having a particle diameter of less than 45 μm in the content of less than 0.5 wt %, based on the total weight of the aluminosilicate particles.

5. The superabsorbent polymer composition according to claim 1, wherein the organic acid includes one or more selected from the group consisting of citric acid, fumaric acid, maleic acid and lactic acid.

6. The superabsorbent polymer composition according to claim 1, wherein the aluminosilicate particles on which organic acid is supported further comprise silica.

7. The superabsorbent polymer composition according to claim 1, wherein the aluminosilicate particles on which organic acid is supported are included in the content of 1 to 10 parts by weight, based on 100 parts by weight of the superabsorbent polymer.

8. The superabsorbent polymer composition according to claim 1, wherein the removal rate of ammonia gas is 80% or more, when 1 g of the superabsorbent polymer composition of a dry state is put in a bag of 3 L volume, and then, 100 ppm of ammonia gas is introduced into the bag, and after 30 minutes, the removal rate of ammonia gas is measured.

9. The superabsorbent polymer composition according to claim 1, wherein the removal rate of ammonia gas is 90% or more, when 1 g of the superabsorbent polymer of a dry state is swollen with 30 g of a saline solution (0.9 wt % NaCl solution) for 30 minutes and 0.5 g of the superabsorbent polymer of a swollen gel state is put into a bag of 3 L volume, and then, 500 ppm of ammonia gas is introduced into the bag, and after 30 minutes, the removal rate of ammonia gas is measured.

* * * * *